United States Patent [19]
Owyang

[11] Patent Number: 5,929,035
[45] Date of Patent: Jul. 27, 1999

[54] METHODS OF TREATING INTESTINAL DISORDERS

[75] Inventor: Chung Owyang, Ann Arbor, Mich.

[73] Assignee: Regents of the University of Michigan, Ann Arbor, Mich.

[21] Appl. No.: 09/059,845

[22] Filed: Apr. 14, 1998

[51] Int. Cl.[6] .......................... A61K 38/00; A61K 38/02; C07K 5/00; C07K 7/00
[52] U.S. Cl. .............................. 514/13; 530/300; 530/326
[58] Field of Search ................................ 514/13; 530/300, 530/326

[56] References Cited

U.S. PATENT DOCUMENTS 5,821,219  10/1998  Grandy et al. .............................. 514/2

*Primary Examiner*—Avis M. Davenport
*Attorney, Agent, or Firm*—Medlen & Carroll, LLP

[57] ABSTRACT

Methods and compositions are described for the treatment of intestinal disorders, and, more specifically, for improving motility in the colon in humans and animals. Compositions comprising neuropeptides are administered to humans and animals having symptoms of post-operative ileus.

11 Claims, 7 Drawing Sheets

FIG. 1A STOMACH BODY
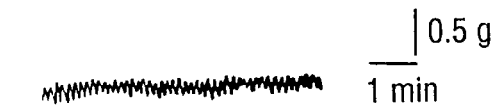
FIG. 1B JEJUNUM
FIG. 1C ILEUM
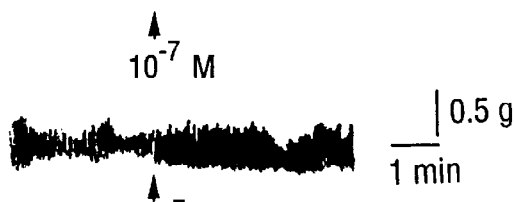
FIG. 1D PROXIMAL COLON
DISTAL COLON
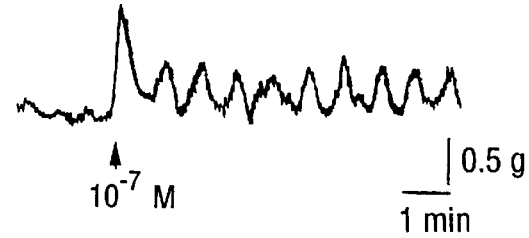

LONGITUDINAL MUSCLE

CIRCULAR MUSCLE

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:1:

Phe Gly Gly Phe Thr Gly Ala Arg Lys Ser Ala Arg Lys Leu Ala Asn
1            5                   10               15

Gln (2) INFORMATION FOR SEQ ID NO:2:

(i) SEQUENCE CHARACTERISTICS:
        (A) LENGTH: 3 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:2:

Arg Gly Asp
1

(2) INFORMATION FOR SEQ ID NO:3:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:3:

Phe Gly Gly Phe Thr
1            5

(2) INFORMATION FOR SEQ ID NO:4:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:4:

Lys Leu Ala Asn Gln
1            5

METHODS OF TREATING INTESTINAL DISORDERS

FIELD OF THE INVENTION

The invention generally relates to the treatment of intestinal disorders, and, more specifically, to treatment directed at improving motility in the colon in humans and animals, including but not limited to, treatment for humans and animals having symptoms of post-operative ileus.

BACKGROUND

A. Post-operative Ileus

Post-operative ileus is a common clinical problem for which there is no effective treatment. Following an operation, gastrointestinal motor failure ensues for several days; food and fluids are not tolerated, and no flatus or stool is passed per rectum. Studies of motor activity in animals have shown that contractions return first in the small intestine 3 to 6 hours after laparotomy, in the stomach after 24 hours and in the colon after several days (Arch Surg 1977; 112:203, Surgery 1978; 84:527). Analogues human studies confirm that the colon is slowest to recover (Gut 1975; 16:689, Ann Surg 1986; 203:574). Furthermore, motility patterns do not return entirely to normal as soon as contractions return so that normal digestive function is delayed. This reduces the rate of patient mobilization and recovery, and may also reduce or delay absorption of drugs administered by the GI tract. As a result, post operative ileus generally prolongs length of stay in the hospital.

The factors influencing the duration of ileus are varied. Manipulation of the abdominal organs delays return of function longer than laparotomy alone. Chemical or physical irritants in the peritoneal cavity such as bile, blood or talc delay recovery even longer. Bowel dilatation from gas and fluid accumulation activates visceral afferents and an inhibitory reflex arc (Scan J Gastro 1979; 14:101). Somatic inhibitory reflexes are activated at the beginning of a laparotomy when the parietal peritoneum is entered. The mediator involved in post-operative ileus are unknown. Adrenergic inhibition has been considered to be the cause; however, it does not explain why the process lasts several days. Plasma concentrations of catecholamines are elevated after general anesthesia and laparotomy, but the benefit of adrenalectomy, demalullation, or adrenergic antagonists in reducing ileus is controversial (Arch Surg 1977; 112:203).

In addition to the effects of surgery, the residual effects of anesthetic agents, and particularly by opioids administered for post-operative pain relief may also play a role in the development of post-operative ileus. Therefore, currently it is believed that although stimulation of the sympathetic nervous system following a laparotomy may play a role, mechanisms other than spinal reflexes (through the sympathetic nervous system) contribute significantly to the development and maintenance of post-operative ileus (Gastro 1975; 68:466).

Pharmacological approach in the treatment of post-operative ileus has been rather disappointing. Cisapride, a synthetic substituted piperidinyl benzamide is commercially available for treating gastric stasis syndrome. However, the efficacy of the drug has come into question. A randomized, double-blind, placebo-controlled study in patients undergoing elective upper gastrointestinal or colonic surgery showed no difference between the cisapride-treated and placebo-treated patients in shortening the duration of post-operative ileus. See B. Hallerback et al., "Cisapride in the Treatment of Post-Operative Ileus," *Aliment Pharmocol. Ther.* 5:503 (1991).

The drug cholecystokinin (CCK) has also been tested on patients with post-operative ileus. However, in a randomized, double-blind trial, no differences were found between the CCK-treated group and the placebo group. See J. Frisell et al., "The Effect of Cholecystokinin on Post-Operative Bowel Function," *Acta Chir. Scand.* 151:557 (1985).

The effects of dihydroergotamine (DHE) on post-operative ileus has also been examined in patients following major abdominal surgery. There were no significant differences between DHE-treated patients and controls in the duration of post-operative ileus. See J. Thorup et al., "DiHydro Ergotamine in Post-Operative Ileus," *Clin. Pharmacol. Ther.* 34:54 (1983).

What is needed is a treatment approach that is effective in shortening the duration of post-operative ileus. Such an approach should be specific with minimum involvement of organs other than the colon.

B. Constipation

Constipation is one of the most common clinical problems in the western world. In the United States, 368 million dollars were spent for laxatives in 1982 (Am J Gastro 1985; 80:303); some are used unnecessarily, and many may be harmful. No data exist regarding additional costs generated as a result of medical evaluations, diagnostic studies, surgery, and absences from work relating to constipation.

Constipation may be conceptually regarded as disordered movement through the colon because, with few exceptions, transit through the more proximal regions of the GI tract are normal. From a pathophysiologic viewpoint, impairment of large intestine transit can occur because of a primary motor disorder, in association with a large number of diseases, or as a side effect of many drugs. However, the vast majority of constipated patients have no obvious cause to explain their symptoms but are presumed to have an underlying disorder of colonic or anorectal function.

In addition to dietary ad behavioral approaches, pharmacologic therapy remains the main stay in the treatment of chronic constipation and vast amounts are consumed in the western world, especially by elderly persons. Laxatives are classified into five groups on the basis of their presumed mode of action. These include bulk forming laxatives, emollient laxatives, hyperosmolar laxatives, saline laxatives, and stimulant laxatives. Except for the bulk laxatives, routine use of these agents over long periods of time should be discouraged because of potential serious side effects on the colonic nervous and muscular systems.

Recently prokinetic agents that stimulate gastrointestinal motor activity to enhance transit of intraluminal contents have been used to treat chronic constipation. Both metoclopramide and cisapride which have been used to treat upper GI motor disorders exert little effect on colonic motility and are not very effective in constipated patients (Functional disorders of the GI tract, In: Cohen S, Soloway R D eds. New York: Churchill Livingstone, 1987:95). Ideally an agent which is derived from a naturally occurring substance in the GI tract, which stimulate colonic peristalsis would be ideal in the treatment of colonic constipation.

C. Irritable Bowel Syndrome (IBS)

IBS is the most prevalent digestive disease accounting for 12% of visits to primary care physicians and 28% of referrals to gastroenterologists (Gastroenterology 1987; 92:1282). Over 2 million prescriptions are written for IBS (Gastroenterology 1990; 99:409).

IBS is a heterogeneous disorder with distinct symptom presentations. Abdominal pain and irregular bowel habits are the major complaints. IBS patients with predominant diarrhea symptoms only account for 20% of the IBS patients. Most other IBS patients present with either constipation or constipation alternating with diarrhea. With constipation, stools usually are hard and may be scybalous or pellet-like. Long periods of straining may be required for fecal evacuation. Constipation can persist for weeks to months, interrupted by brief periods of diarrhea. Other frequent associated symptoms are abdominal cramps, gas and bloating.

Regulation of bowel function is an important aspect of the treatment of constipation, abdominal cramps, gas and bloating. Treatment with increased dietary fiber and/or osmotic laxatives may promote more rapid transit and relieve constipation and functional obstruction. However control trials indicate that fiber supplementation is no better than placebo for the IBS population as a whole (Gastroenterology 1988; 95:232), however some constipated patients may respond to intensive fiber treatment. Prokinetic agents such as cisapride has been shown to increase stool frequency and accelerate whole gut transit in IBS patients (Progr Med 1987; 43:121) and may provide some clinical benefits to constipation IBS patients (J Clin Gast 1991; 13:49, Aliment Pharmacol Ther 1997; 11:387). However, since cisapride acts primarily on the upper gut, subsequent clinical experience has been disappointing in IBS patients with severe constipation. An agent which acts specifically to initiate peristalsis in the colon should provide better clinical response.

SUMMARY OF THE INVENTION

The invention generally relates to the treatment of intestinal disorders, and, more specifically, to treatment directed at improving motility in the colon in humans and animals, including but not limited to, treatment for humans and animals having symptoms of post-operative ileus. The present invention contemplates treatment of humans and animals having intestinal disorders with neuropeptides, neuropeptide derivatives and mimetics. In particular, the present invention contemplates treatment with a neuropeptide recently isolated from porcine brain, named Orphanin FQ (hereinafter "OFQ") having the primary structure: Phe-Gly-Gly-Phe-Thr-Gly-Ala-Arg-Lys-Ser-Ala-Arg-Lys-Leu-Ala-Asn-Gln (SEQ ID NO:1).

It is not intended that the present invention be limited by the nature of the formulation of the above-named peptide or by the route of delivery. A variety of formulations (tablets, suppositories, solutions, etc.) are contemplates along with various routes of administration (oral, rectal, intravenous, etc.).

While the present invention can be used with particular success with humans having post-operative ileus, it is not intended that the present invention be limited to only particular intestinal disorders. The present invention contemplates treatment of patients with constipation as well as irritable bowel syndrome (gas and bloating). In one embodiment, the present invention contemplates a method of treatment, comprising: a) providing: i) a human having symptoms of an intestinal colonic disorder; and ii) a therapeutic preparation comprising a neuropeptide having the amino acid sequence of SEQ ID NO:1; and b) administering said therapeutic preparation to said human.

It is also not intended that the present invention be limited to only humans. For example, animals such as horses are known to suffer from post-operative ileus. Indeed, it is a common and serious complication of colic surgery in the horse. See J. N. King and E. L. Gerring, "The Action of Low Dose Endotoxin on Equine Bowel Motility," *Equine Vet. J.* 23:11 (1991). It is therefore contemplated that the OFQ peptides of the present invention can be used for treatment of animals, including but not limited to horses.

In another embodiment, the present invention contemplates a method of treatment, comprising: a) providing: i) an animal having symptoms of an intestinal disorder; and ii) a therapeutic preparation comprising a neuropeptide having the amino acid sequence of SEQ ID NO:1; and c) administering said therapeutic preparation to said animal.

DESCRIPTION OF THE DRAWINGS

FIGS. 1A–D are graphs showing the effects of OFQ ($10^{-7}$ M) on contractility of the longitudinal muscle in rat GI tract.

DEFINITIONS

Figure 2A:
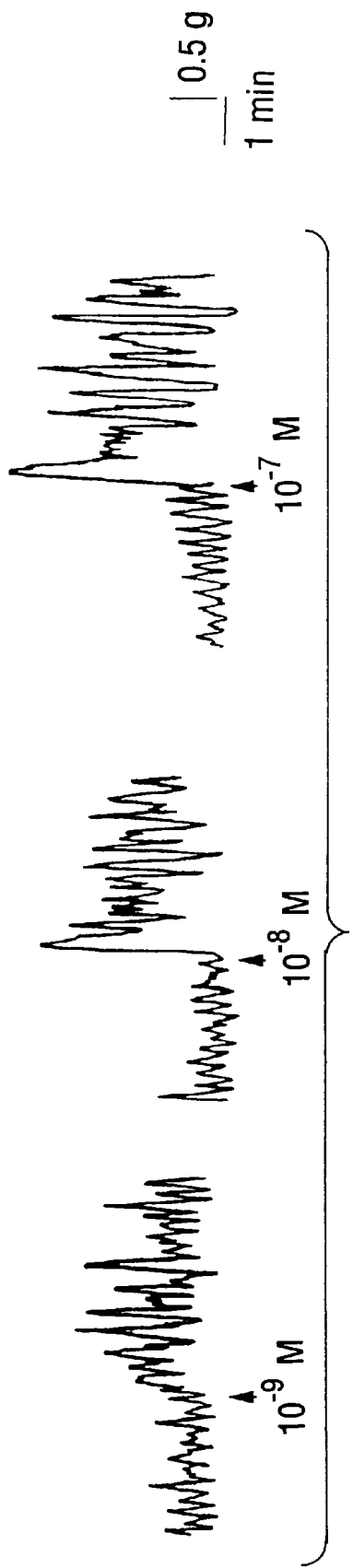
FIGS. 2A and 2B are graphs showing the effects of OFQ ($10^{-9}$–$10^{-7}$ M) on the contractile activity of the longitudinal muscle strips obtained from the proximal and the distal colon in rats (M±SE, n=4).

As used herein "post-operative ileus" is meant to indicate lack of motility of the colon following surgery. Knowledge of the patho-physiological behaviour present in the colon is the deciding factor for a reliable differential diagnosis of mechanical or paralytic ileus. A quick and sure diagnosis can be got with irrigoscopy (barium enema). In paralytic ileus, a radical change in the function of the right colon is present; instead of resorption, exudation and paralysis have taken place. Barium enema shows this behaviour; the left colon stays contracted, the contrast medium passes easily into the right colon, where it mixes with the fluid levels. This picture is proof of paralytic ileus. A completely different picture is to be found in mechanical ileus of the small intestine; the small intestine is gas-inflated, with fluid levels, and passes nothing on to the colon which, therefore, is contracted in its whole length. This picture also is diagnostic. Barium enema is already known in the diagnosis of mechanical ileus of the large intestine. It can also be used in the diagnosis of paralytic enterocolitia (without diarrhoea) in childhood and old age. In the case of post-operative early ileus it gives a quick and sure differential diagnosis.

DESCRIPTION OF THE INVENTION

The invention generally relates to the treatment of intestinal disorders, and, more specifically, to treatment directed at improving motility in the colon in humans and animals, including but not limited to, treatment for humans and animals having symptoms of post-operative ileus. As noted above, the present invention contemplates treatment with (A) neuropeptides, (B) peptide derivatives and (C) mimetics. All of these compounds are contemplated in a variety of (D) formulations.

A. The OFQ Neuropeptide

The present invention contemplates treatment of intestinal disorders with OFQ, a neuropeptide recently isolated from porcine brain which is believed to be an endogenous ligand for an opioid-like, G protein-coupled receptor. See R. K. Reinscheid et al.,"Orphanin FQ: a neuropeptide that activates an opioidlike G protein- coupled receptor," *Science* 270:792 (1995). Another group isolated this peptide from rat brain and called it Nociceptin, because it seemed to increase reaction to pain. See J-C. Meunier et al.,"Isolation and structure of the endogenous agonist of opioid receptor-like ORL1 receptor," *Nature* 377:532 (1995). Its corresponding receptor, OFQ receptor or opioid receptor like-1 (ORL-1receptor, exhibited 50% to 60% sequence identity with cloned opioid receptors. See C. Mollereau et al., "ORL1, a novel member of the opioid receptor family cloning, functional expression and localization," FEBS Lett 341:3338 (1994).

Despite its similarity to $\mu$-, $\delta$-, $\kappa$-opioid receptors, OFQ receptor does not bind with any known opioid peptides or ligands. It shares several sequence motifs with opioid peptides known to be important for biologic activity. However, OFQ does not show any activity at the opioid receptor. OFQ receptor transcripts are found in mouse and rat central nervous system, as well as in peripheral organs, such as intestine, vas deferens, and spleen. See J. Wang et al., "cDNA cloning of an orphan opiate receptor gene family member and its splice variant," *FEBS Lett* 348:7579 (1994).

B. Peptide Derivatives

It is not intended that the present invention be limited only the peptides having the primary structure of:: Phe-Gly-Gly-Phe-Thr-Gly-Ala-Arg-Lys-Ser-Ala-Arg-Lys-Leu-Ala-Asn-Gln (SEQ ID NO:1). A variety of peptide derivatives are contemplated, including peptides where additional amino acids are added to the carboxy terminus. Alternatively, peptides are contemplated where amino acids are added to the amino terminus. The present invention contemplates peptides having the above primary structure wherein certain amino acids are substituted or deleted. Finally, the present invention contemplates peptide derivatives having a combination of the above-described changes, such as where amino acids are added to both the amino and carboxy termini.

In another embodiment, the present invention also contemplates peptides protected from endoprotease degradation by the substitution of L-amino acids in said peptides with their corresponding D-isomers. It is not intended that the present invention be limited to particular amino acids and particular D-isomers. This embodiment is feasible for all amino acids, except glycine; that is to say, it is feasible for all amino acids that have two stereoisomeric forms. By convention these mirror-image structures are called the D and L forms of the amino acid. These forms cannot be interconverted without breaking a chemical bond. With rare exceptions, only the L forms of amino acids are found in naturally occurring proteins.

C. Mimetics

Compounds mimicking the necessary conformation for recognition and docking to the receptor binding to the peptides of the present invention are contemplated as within the scope of this invention. For example, mimetics of the OFQ peptides are contemplated. A variety of designs for such mimetics are possible. For example, cyclic OFQ peptides, in which the necessary conformation for binding is stabilized by nonpeptides, are specifically contemplated. U.S. Pat. No. 5,192,746 to Lobl, et al, U.S. Pat. No. 5,169,862 to Burke, Jr., et al, U.S. Pat. No. 5,539,085 to Bischoff, et al, U.S. Pat. No. 5,576,423 to Aversa, et al, U.S. Pat. No. 5,051,448 to Shashoua, and U.S. Pat. No. 5,559,103 to Gaeta, et al, all hereby incorporated by reference, describe multiple methods for creating such compounds.

Synthesis of nonpeptide compounds that mimic peptide sequences is also known in the art. Eldred, et al, (*J. Med. Chem.* 37:3882 (1994)) describe nonpeptide antagonists that mimic SEQ ID NO:2 the Arg-Gly-Asp sequence. Likewise, Ku, et al, (*J. Med. Chem.* 38:9 (1995)) give further elucidation of the synthesis of a series of such compounds. Such nonpeptide compounds that mimic OFQ peptides are specifically contemplated by the present invention.

The present invention also contemplates synthetic mimicking compounds that contain the relevant peptide sequence, as well as multimeric compounds that repeat the relevant peptide sequence. In one embodiment of the present invention, it is contemplated that the relevant peptide sequence is SEQ ID NO:3 Phe-Gly-Gly-Phe-Thr; in another embodiment, the relevant peptide sequence is SEQ ID NO:4 Lys-Leu-Ala-Asn-Gln. As is known in the art, peptides can be synthesized by linking an amino group to a carboxyl group that has been activated by reaction with a coupling agent, such as dicyclohexylcarbodiimide (DCC). The attack of a free amino group on the activated carboxyl leads to the formation of a peptide bond and the release of dicyclohexylurea. It can be necessary to protect potentially reactive groups other than the amino and carboxyl groups intended to react. For example, the $\alpha$-amino group of the component containing the activated carboxyl group can be blocked with a tertbutyloxycarbonyl group. This protecting group can be subsequently removed by exposing the peptide to dilute acid, which leaves peptide bonds intact. With this method, peptides can be readily synthesized by a solid phase method by adding amino acids stepwise to a growing peptide chain that is linked to an insoluble matrix, such as polystyrene beads. The carboxyl-terminal amino acid (with an amino protecting group) of the desired peptide sequence is first anchored to the polystyrene beads. The protecting group of the amino acid is then removed. The next amino acid (with the protecting group) is added with the coupling agent. This is followed by a washing cycle. The cycle is repeated as necessary.

In one embodiment, the mimetics of the present invention are peptides having sequence homology to the above-described OFQ peptides. One common methodology for evaluating sequence homology, and more importantly statistically significant similarities, is to use a Monte Carlo analysis using an algorithm written by Lipman and Pearson to obtain a Z value. According to this analysis, a Z value greater than 6 indicates probable significance, and a Z value greater than 10 is considered to be statistically significant. W. R. Pearson and D. J. Lipman, Proc. Natl. Acad. Sci. (USA), 85:2444–2448 (1988); D. J. Lipman and W. R. Pearson, Science, 227:1435–1441 (1985). In the present invention, synthetic polypeptides useful in therapy are those peptides with statistically significant sequence homology and similarity (Z value of Lipman and Pearson algorithm in Monte Carlo analysis exceeding 6).

D. Formulations

It is not intended that the present invention be limited by the particular nature of the therapeutic preparation. For example, such compositions can be provided together with physiologically tolerable liquid, gel or solid carriers, diluents, adjuvants and excipients. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

Such compositions are typically prepared as liquid solutions or suspensions, or in solid forms. Oral formulations will commonly include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%–95% of active ingredient, preferably 2%–70%.

The compositions are also prepared as injectables, either as liquid solutions or suspensions; solid forms suitable for solution in, or suspension in, liquid prior to injection may also be prepared. Additional formulations which are suitable for other modes of administration, such as topical administration, include salves, tinctures, creams, lotions, and suppositories. Traditional binders, carriers and excipients may include, for example, polyalkylene glycols or triglycerides.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); mM (millimolar); N (Normal); mol (moles); mmol (millimoles); $\mu$mol (micromoles); nmol (nanomoles); g (grams); mg (milligrams); $\mu$g (micrograms); L (liters); ml (milliliters); $\mu$l (microliters); cm (centimeters); mm (millimeters); $\mu$m (micrometers); nm (nanometers); ° C. (degrees Centigrade); mAb (monoclonal antibody); MW (molecular weight); PBS (phophate buffered saline); U (units); d(days).

Materials

Atropine, apamin, benzalkonium chloride, carbachol, diaminobenzidine, guanethidine, hemicholinium-3, hexamethonium, indomethacin, naloxone, phentolamine, propranolol, tetrodotoxin (TTX) and veratridine were obtained from Sigma Chemical Co. (St. Louis, Mo.). Vasoactive intestinal polypeptide (VIP) antagonist ([p-chloro-D-Phe[6], LEU [17]]-VIP) was obtained from Bachem (Torrance, Calif.). Substance P antagonist ([D-Pro[4], D-Trp7.9]-substance P 4-11) was obtained from Peninsular (Belmont, Calif.). NG-nitro-L-arginine methyl ester (L-NAME) and methysergide were obtained from Research Biochemicals International (Natick, Mass.). Anti-rabbit IgG and the avidin-biotin labeled kit (Vectastain ABC kit) were obtained from Vector Laboratories (Burlingame, Calif.). OFQ was obtained from Phoenix Pharmaceuticals, INC. (Mountain View, Calif.). $^3$H-choline chloride was obtained from American Radiolabelled Chemicals Co. (St. Louis, Mo.).

EXAMPLE 1

In this motility study, Male Sprague-Dawley (SD) rats (body wt; 230–250 g) were fasted overnight and euthanized. Longitudinal and circular muscle strips were isolated from the stomach body, jejunum, ileum, proximal colon and distal colon. Muscle strips (10 mm in length and 3 mm in width) were suspended between two platinum electrodes in a 30 mL organ bath filled with Krebs-Henseleit buffer (KHB) of the following composition: 118 mM NaCl, 4.8 mM KCl, 2.5 mM $CaCl_2$, 25 mM $NaHCO_3$, 1.2 mM $KH_2PO_4$, 1.2 mM $MgSO_4$, 11 mM glucose and 0.1% bovine serum albumin. KHB solution was continuously gassed with 95% $O_2$-5% $CO_2$ and maintained at 37° C. and pH 7.4. Mechanical activity was recorded on a polygraph through isometric transducers. Muscle strips were stretched in 1-mm increments and repeatedly exposed to $10^{-6}$ M carbachol to determine $L_O$, the length at which the maximal active tension response developed. The resting tension was kept constant during the equilibration period. Experiments were started after a 60-min equilibration period. Dose-response curves were constructed after applying OFQ ($10^{-9}$ M–10–6 M) to longitudinal and circular muscle strips from various regions of gastrointestinal tract. Doses of OFQ were applied at 20-min intervals to prevent tachyphylaxis.

Figure 2B:
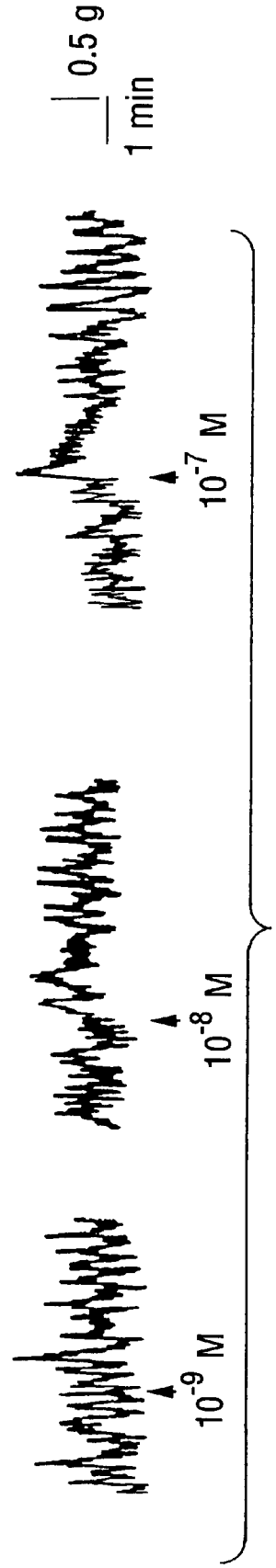

In vitro studies using longitudinal and circular muscle from various regions of rat gastrointestinal tract revealed that OFQ ($10^{-9}$ M–$10^{-6}$M) induced contractions only in the colon (FIG. 1). Contractions could be induced with a threshold OFQ concentration of $10^{-9}$ M. Contractions induced by OFQ ($10^{-7}$M) in the longitudinal muscle of the proximal colon were 2–3 fold greater than those in the distal colon (FIG. 2). OFQ up to a concentration of $10^{-6}$ M failed to elicit significant contractions in the longitudinal and circular muscle layer from the stomach and small intestine.

OFQ caused various types of muscular contractions in rat proximal colon. OFQ ($10_{-8}$M) caused only a slight initial contraction followed by a pronounced phasic response in 11 strips of 87 tested (12.6%). OFQ ($10^{-8}$M) caused a potent initial phasic contraction followed by a phasic response in 53 strips of 87 tested (60.9%). OFQ ($10^{-8}$M) caused a smaller initial contraction followed by a gradually increasing phasic response in 23 strips of 87 tested (26.4%). Strong phasic contractions persisted more than 10–15 min until washing.

OFQ-induced contractions were further investigated in the proximal colon. OFQ ($10^{-9}$ M–$10^{-6}$M) induced contractions in the longitudinal and circular muscle of the rat proximal colon in a dose-dependent manner. The maximal effect was elicited with $10^{-7}$ M OFQ at 278%±24% increase of basal contraction in longitudinal muscles and 215%±32% increase of basal contraction in circular muscles, respectively. Contractions induced by OFQ at $10^{-7}$ M and at $10^{-6}$ M were not significantly different.

EXAMPLE 2

To investigate the neural pathways responsible for the contractile action of OFQ, the effects of various antagonists on OFQ-induced contractions were examined. Muscle strips were preincubated with each antagonists for 10 min, followed by incubation with OFQ. The chemicals used were as follows: atropine ($10^{-6}$ M), hexamethonium ($10^{-4}$ M), naloxone ($10^{-5}$ M), indomethacin ($10^{-5}$ M), methysergide ($3 \times 10^{-5}$ M), VIP antagonist ($5 \times 10^{-6}$ M), substance P antagonist ($10^{-5}$ M), L-NAME ($10^{-4}$ M), apamin ($10^{-6}$ M), guanethidine ($10^{-5}$ M), phentolamine ($10^{-6}$ M), propranolol ($10^{-6}$ M) and TTX ($10^{-7}$ M). In addition, we used veratridine ($5 \times 10^{-6}$–$5 \times 10^{-5}$ M) to inactivate neurotransmission within the myenteric plexus. It has been demonstrated that higher concentrations of veratridine (>5 ×10–6 M) inactivates neurons due to large depolarization of the myenteric neurons.

Figure 5:
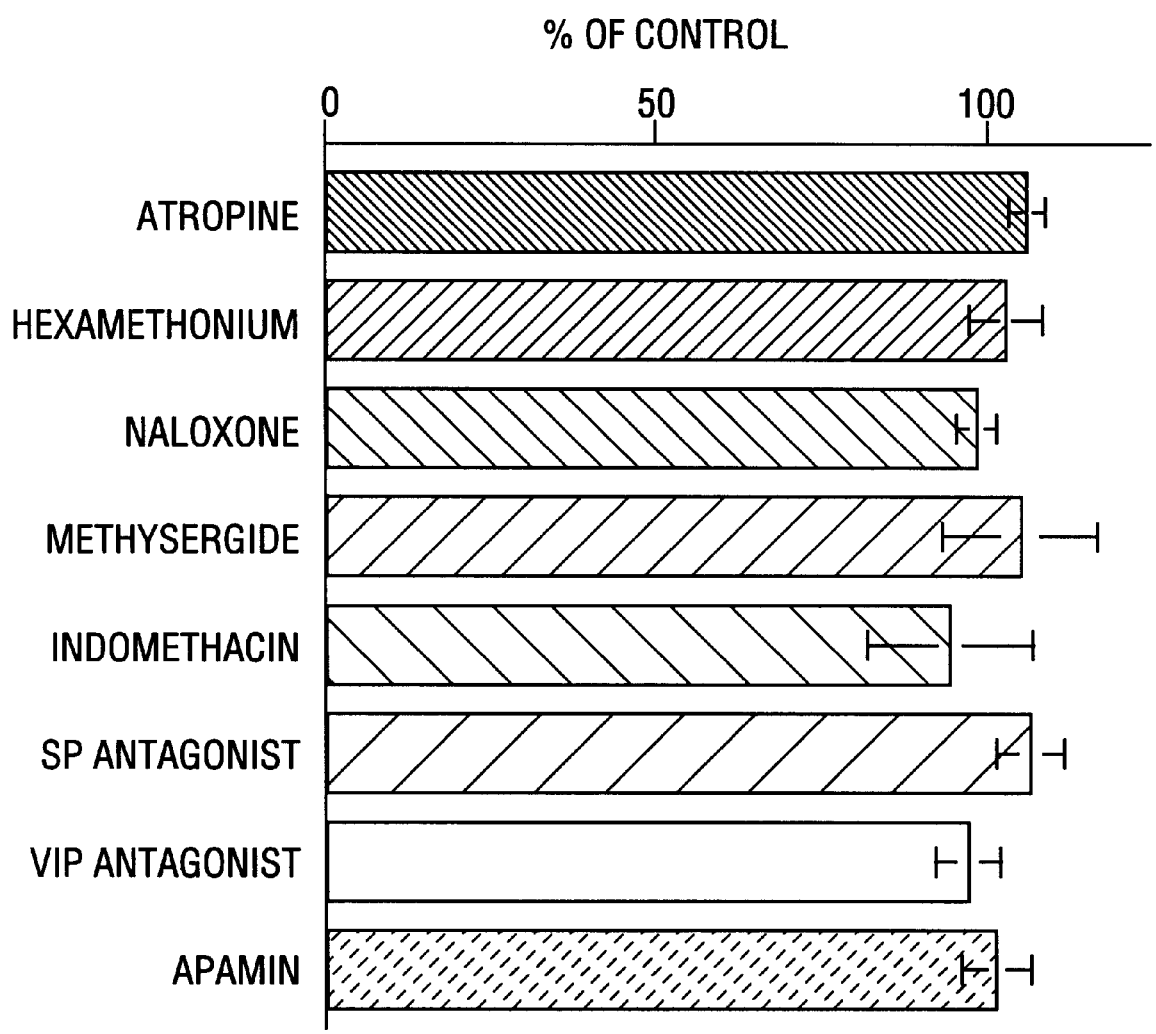
FIG. 5 is a bar graph showing the effects of atropine ($10^{-6}$ M), hexamethonium ($10^{-4}$ M), naloxone ($10^{-5}$ M), methysergide ($3\times10^{-5}$ M), indomethacin ($10^{-5}$ M), substance P antagonist ($10^{-5}$ M), and VIP antagonist ($5\times10^{-6}$ M) on OFQ ($10^{-8}$ M)-induced contractions in longitudinal muscle from rat proximal colon.
Figure 6:
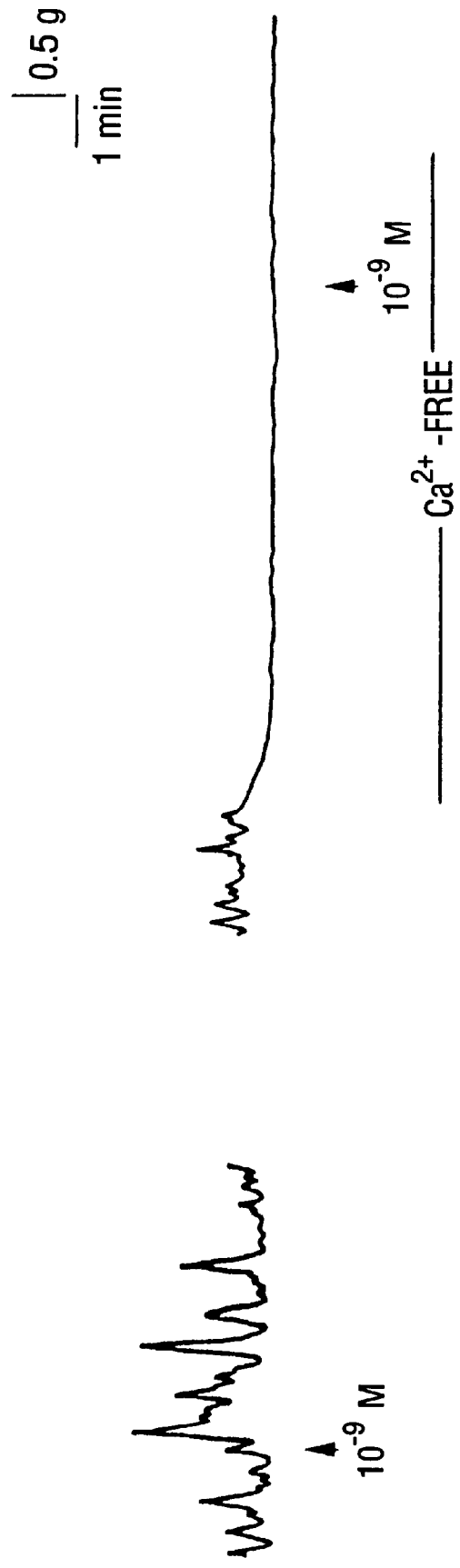
FIG. 6 shows graphs measuring the effects of Ca2+-free medium on OFQ ($10^{-7}$ M)-induced contractions in longitudinal muscle in rat proximal colon. OFQ-induced contractions were abolished by Ca2+-free medium.

Pretreatment with atropine ($10^{-6}$ M), hexamethonium ($10^{-4}$ M), naloxone ($10^{-5}$ M), indomethacin ($10^{-5}$ M), methysergide ($3 \times 10^{-5}$ M), and substance P antagonist (10–5 M) did not affect OFQ ($10^{-8}$ M)-induced contractions (FIG. 5). In contrast, $Ca^{2+}$-free medium abolished OFQ-induced contractions in the rat proximal colon (FIG. 6). The concentration of each antagonist was shown to be effective in reducing contractions induced by their respective agonists (data not shown). These observations suggest that OFQ is acting via a $Ca^{2+}$-dependent pathway that is not mediated by acetylcholine, opiates, 5-HT, prostaglandins, and substance P.

Figures 3A, 3B, 3C, 3D:
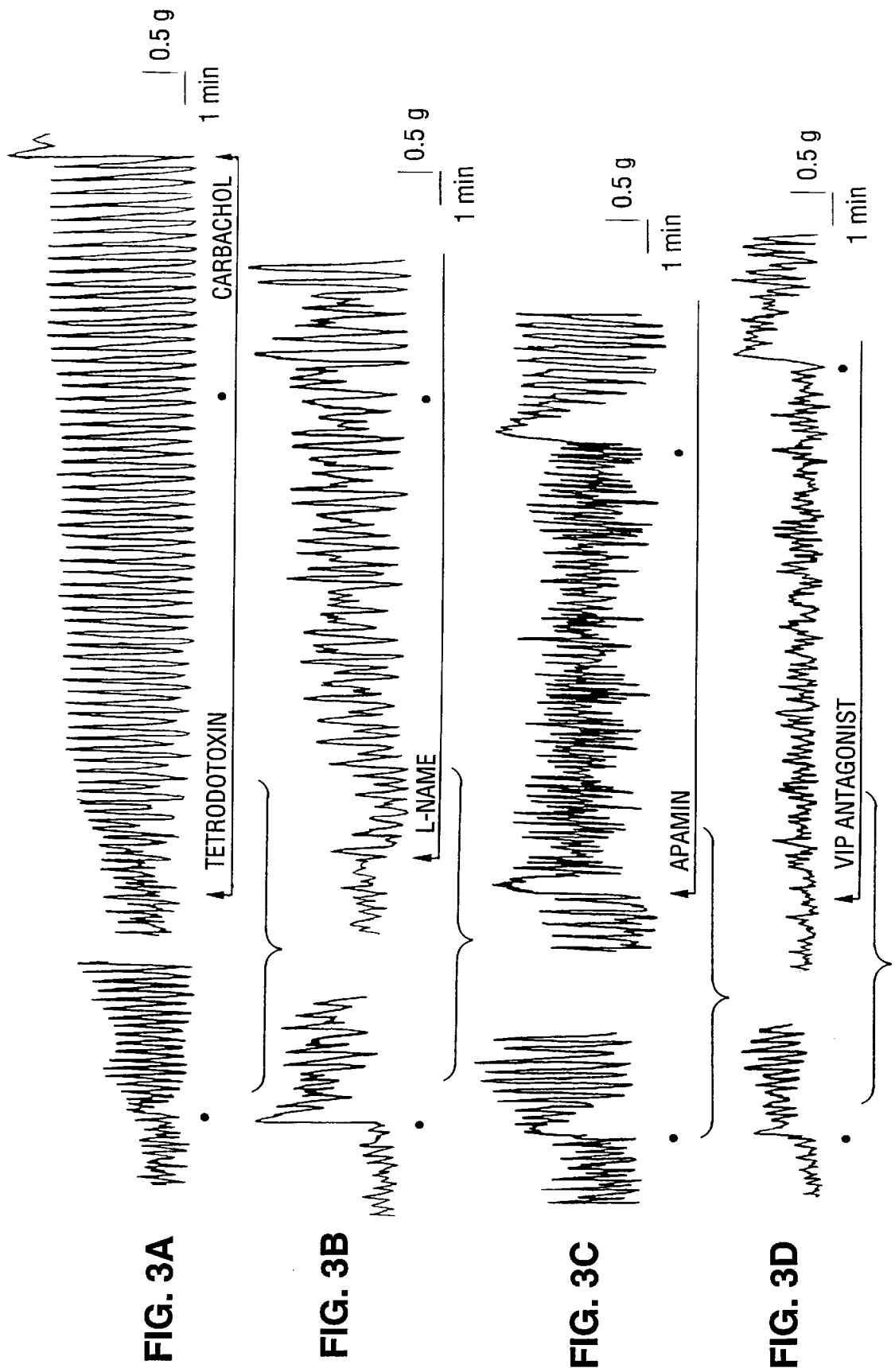
FIG. 3 shows the effects of TTX ($10^{-7}$ M), 1-NAME ($10^{-4}$ M), apamin ($10^{-6}$ M), and VIP antagonist ($5\times10^{-6}$ M) on OFQ ($10^{-8}$ M)-induced contractions in longitudinal muscle from rat proximal colon. Increased baseline contractions after exposure to OFQ are represented by ● and shown on the left. On the right, contraction of muscle strips after preincubation with various antagonists, followed by treatment with OFQ.
Figure 7:
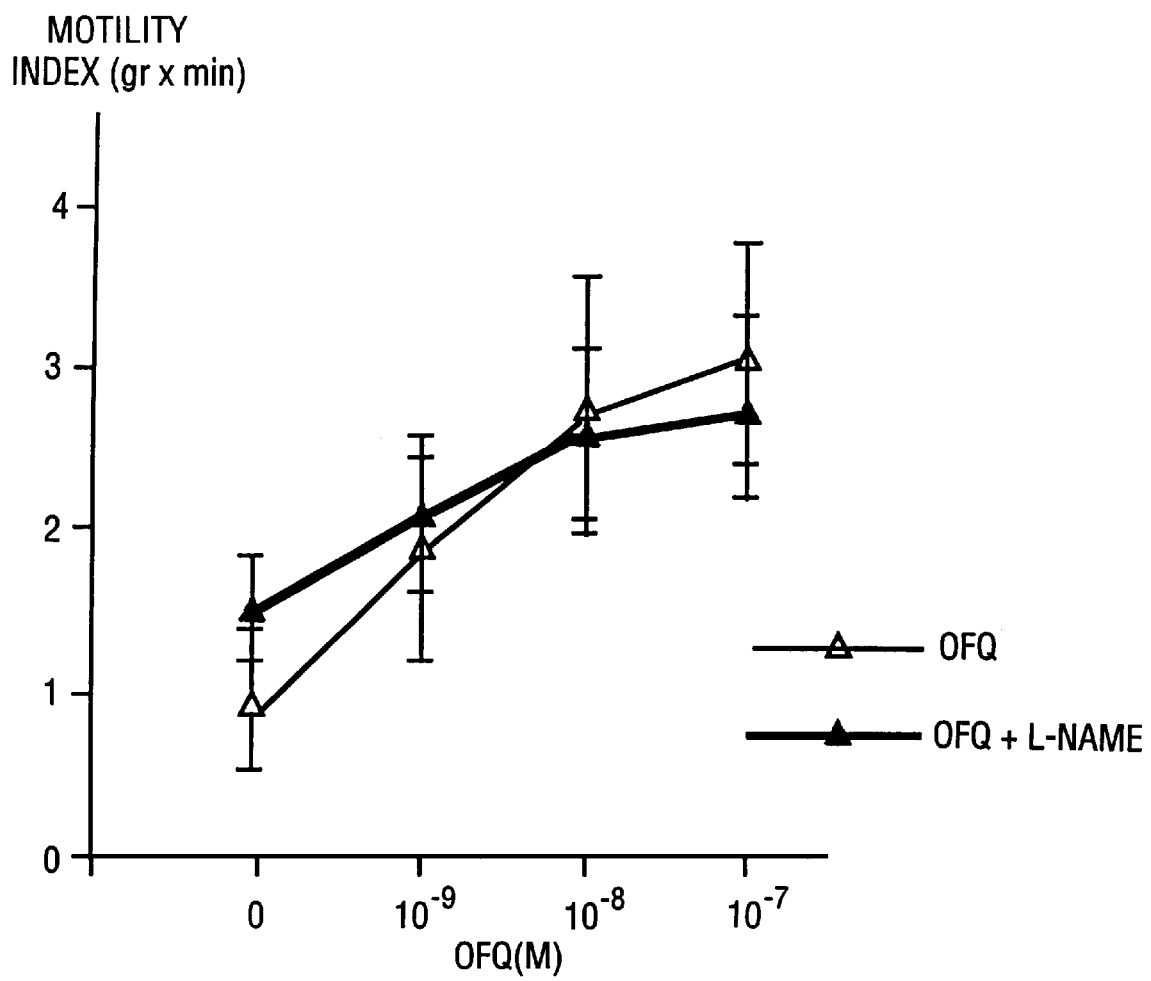
FIG. 7 is a graph showing the effects of L-NAME ($10^{-4}$ M) on OFQ ($10^{-9}$–$10^{-7}$ M) induced contractions in longitudinal muscle from the rat proximal colon.

Nitric oxide (NO), vasoactive intestinal polypeptide (VIP), and adenosine triphosphate (ATP) are known to cause relaxation in the rat colon. Inhibition of the release of these neurotransmitters could potentially cause contractions. To investigate if the action of OFQ was mediated by inhibiting any of these three neurotransmitters, three antagonists were assessed. L-NAME and apamin, NO and ATP antagonists, respectively, enhanced spontaneous contractions in the proximal colon (n=5). However, OFQ-induced contractions were preserved in the presence of L-NAME and apamin (FIGS. 3 and 7), suggesting that OFQ does not act via NO or ATP pathways. In contrast to L-NAME and apamin, VIP antagonist ($5 \times 10^{-6}$ M) had no significant effects on spontaneous contractions in the proximal colon (n=5). VIP antagonist ($5 \times 10^{-6}$ M), which significantly antagonized the action of VIP ($10^{-7}$ M), did not affect OFQ-induced contractions (FIG. 5). Similarly, OFQ-induced contractions were not affected by guanethidine, phentolamine, and propranolol (data not shown).

EXAMPLE 3

It has been recently shown that OFQ has potent inhibitory effects on electrical field stimulation (EFS)-evoked muscular contraction in the mouse vas deferens and guinea pig ileum. See G. Calo et al., "The mouse vas deferens: a pharmacological preparation sensitive to nociceptin," *Eur J Pharmacol* 311 :R3–5 (1996); G. Calo et al., "Pharmacological characterization of nociceptin receptor: an in vitro study," *Can J Physiol Pharmacol* 75:713–718 (1997). To investigate if OFQ affects EFS-evoked muscular contractions in rat GI tract, longitudinal muscle strips obtained from gastric body, ileum and proximal colon were stimulated by EFS (65 V, 0.5 msec, 10 Hz, for 30 sec) in the absence and presence of OFQ ($10^{-9}$ M–$10^{-6}$ M). Muscle strips were pretreated with OFQ ($10^{-9}$ M–$10^{-6}$ M) 10 min before the application of EFS. EFS-evoked muscular contractions were compared between the experiments with and without OFQ pretreatment.

EFS (65 V, 10 Hz, 0.5 msec, for 30 sec) induced a phasic contraction (on-contraction) of the stomach body, a rapid relaxation and a phasic contraction (on-contraction) followed by an off-contraction of the jejunum and a profound relaxation followed by an off-contraction of the proximal colon, respectively. Both of on- and off-contraction were significantly reduced to 10–20% by atropine in stomach, ileum and proximal colon, suggesting the mediation of ACh release. Ten min premeditation with OFQ ($10^{-7}$M) significantly reduced EFS (65 V, 10 Hz, 0.5 msec)-evoked of-contraction in the stomach and on- and off-contraction in ileum, respectively. In contrast, OFQ ($10^{-7}$M) had no inhibitory effects on off-contraction in response to EFS of the proximal colon. OFQ ($10^{-9}$–$10^{-6}$ M) significantly reduced EFS (10 Hz)-evoked muscular contraction in a dose dependent manner in the stomach and ileum, but not in the proximal colon. Maximum effects were observed at OFQ ($10^{-7}$ M), which reduced EFS-evoked muscular contraction to 41.2±8.5% and 85.2±5.6% in the ileum and stomach, respectively.

EXAMPLE 4

This example examined benzalkonium chloride (BAC)-treatment. It has been demonstrated that cationic surfactants, benzalkonium chloride (BAC), can cause nerve damage in the myenteric plexus in rat jejunum and colon. BAC treatment significantly reduced the number of ganglion cells in the myenteric plexus. EFS caused frequency-dependent and TTX-sensitive contractions in vehicle-treated tissues but not BAC-treated tissues. However, carbachol contracted both vehicle- and BAC-treated tissues with the same degree. These previous studies indicate that chronic ablation of the myenteric plexus by serosal application of BAC essentially eliminates neuronally mediated responses without a concomitant alteration in muscle contractility. To investigate if the action of OFQ is mediated via intramural myenteric plexus, BAC (0.1%) was applied to the serosal surface of the proximal colon every 5 min for 30 min and then rinsed off with saline. Saline-treated group served as controls. Two weeks after BAC- or saline-treatment, the longitudinal muscle strips were used for the organ bath experiments.

The area under the curve was calculated using Planix 7 (Sokkia Corporation, Overland Park, Kans.) and expressed as a motility index. The area under the curve of basal contraction was evaluated over 10 min in each experiment. The area under the curve of antagonist-induced contractions and OFQ-induced contractions was also evaluated over 10 min. The motility index was compared between basal contractions and OFQ-induced contractions in each experiment.

In BAC-treated tissues, spontaneous basal muscle contraction was significantly higher compared to those of vehicle-treated tissues, suggesting the removal of tonic inhibitory neuronal pathways after chronic BAC-treatment. EFS (65 V, 0.5 msec, 10 Hz) failed to cause any responses in the muscle strips obtained from BAC-treated rats. In contrast, carbachol ($10^{-6}$ M) contracted both control and BAC-treated tissues with the same degree. This confirmed the previous demonstration that chronic ablation of the myenteric plexus by chronic application of BAC essentially eliminates neuronally mediated responses without a concomitant alteration in muscle contractility. OFQ ($10^{-7}$ M) caused significant contractions of the longitudinal muscle obtained from vehicle-treated rats, whereas OFQ ($10^{-7}$ M) had no contractile effects on the longitudinal muscles obtained from BAC-treated rats.

EXAMPLE 5

This example involves a $^3$H-acetylcholine release study. The above-described functional study raised the possibility that OFQ may inhibit cholinergic transmission in rat GI tract. To obtain the direct evidence, we measured $^3$H-acetylcholine release in response to EFS. Longitudinal muscle strips obtained from gastric body, ileum and proximal colon were preloaded with $^3$H-choline (5 μCi/mL) for 60 min and were suspended between two platinum electrodes and superfused with oxygenated KHB solution at 37° C. at a flow rate of 1 mL/min. The solution contained hemicholinium-3 ($10^{-5}$ M) to prevent the re-uptake of $^3$H-choline. More than 85% of total radioactivity in the superfusate from both stimulated and non-stimulated samples was shown by electrophoresis to be $^3$H—ACh. Before, during and after EFS (65 V, 0.5 msec, 10 Hz for 30 sec), the superfusate was collected every 30 sec and the radioactivity of the sample was determined by counting in a liquid scintillation spectrometer. EFS was applied 3 times every 30 min. There were no significant differences of $^3$H—ACh release among these stimulations. To investigate if OFQ affects $^3$H—ACh release in response to EFS, OFQ ($3 \times 10^{-7}$ M) was superfused 10 min before the third EFS. $^3$H—ACh release in response to the first and second EFS served as controls and mean $^3$H—ACh release in response to EFS was calculated. Percent increase over basal of $^3$H—ACh release in response to EFS was calculated and compared between the control studies and OFQ-pretreatment studies. At the end of the experiments the tissue was solubilized in 1 mL of tissue solubilizer (TS-1, 55° C., 1 hr). After cooling, 50 μL of glacial acetic acid was added to the solubilized tissue and radioactivity was measured to calculate the efflux rate coefficient and the fractional rate.

EFS (10 Hz) caused a significant $^3$H—ACh release in various GI tract; 65.6±7.8% increase over basal in the stomach; 44.7±5.3% increase over basal in the ileum, and 32.3±4.5% increase over basal in the proximal colon (M±SE, n=4). OFQ ($3 \times 10^{-7}$ M) had no effects on basal release of $^3$H—ACh in the stomach, ileum and proximal colon. However, $^3$H—ACh release in response to EFS (10 Hz) was reduced to 44.7±5.8% (M±SE, n=4, p<0.01, by paired t test) and 88.1±4.3% (M±SE, n=4, p<0.05, by paired t test) by OFQ ($3 \times 10^{-7}$ M) in the ileum and stomach, respectively. In contrast, the inhibitory effect of OFQ on EFS-evoked $^3$H—ACh release was not observed in the proximal colon.

EXAMPLE 6

Figure 4:
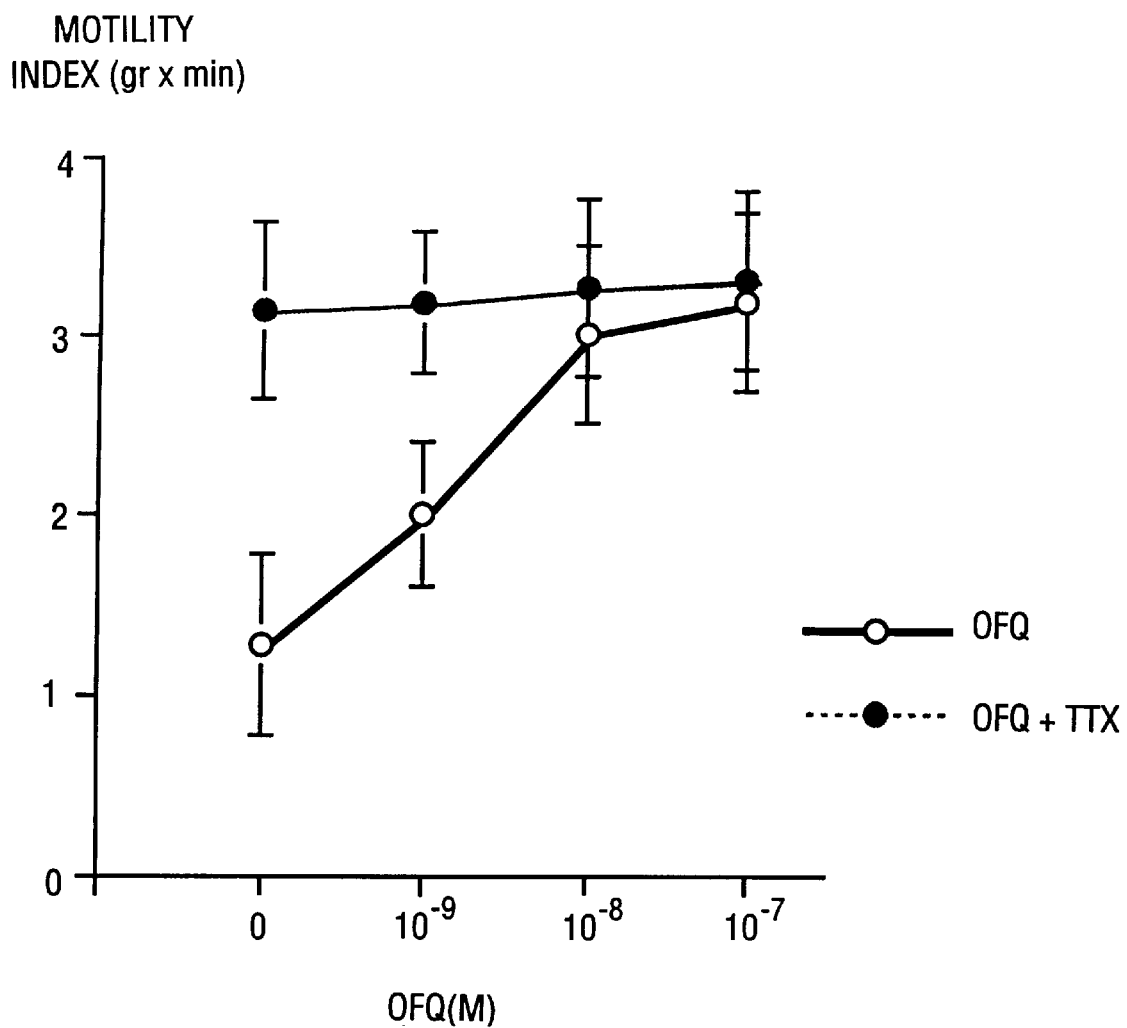
FIG. 4 is a graph showing the effects of TTX ($10^{-7}$ M) on OFQ ($10^{-9}$–$10^{-7}$ M) induced contractions in longitudinal muscle from the rat proximal colon.

To determine if OFQ activity was mediated by neural pathways or if it was a direct myogenic effect, OFQ-induced contractions were examined in the presence of TTX. Spontaneous contractions induced by TTX in the longitudinal muscle layer were enhanced in rat colon, secondary to the removal of inhibitory neural pathways that inhibit the myogenic properties of muscle cells. In the presence of TTX, OFQ failed to elicit additional contractions (FIG. 4). To exclude the possibility that the muscle had achieved maximal contractility induced by TTX and therefore OFQ would not enhance contractions, carbachol ($10^{-6}$ M) was applied after TTX treatment. Carbachol caused further contractions in the presence of TTX (data not shown), suggesting that the muscle had not reached maximal contractility.

EXAMPLE 7

Polyclonal antibodies were generated against the C-terminal end of OFQ. Antibodies were generated by inoculating New Zealand white rabbits several times with the OFQ protein suspended in Freund's adjuvant, followed by rest and bleed procedures. One of the resulting sera for OFQ was affinity-purified using OFQ coupled to a Sepharose-4B-cyanogen bromide column. This antiserum showed no cross-reactivity with any of the known opioid peptides, including ligands for the m-, d-, k-opioid receptors.

Male SE rats were anesthetized with sodium pentobarbital (75 mg/kg, IP) and then perfused through the heart with a solution of 0.9% NaCl and 2.2% $NaNO_2$ (150 mL), followed by Zamboni's fixative (500 mL). The colon was removed, postfixed in the same fixative overnight at (4° C.) and processed for whole-mount analysis. The colon was opened along the mesenteric border, rinsed in 50 mM potassium phosphate-buffered saline (KPBS) and prepared for layer separation. Small, 1 $cm^2$-pieces of tissue were cut flat. The mucosa and submucosa were removed with forceps. The longitudinal muscle layer was peeled away from the circular muscle layer with fine forceps and processed for immunohistochemical examination.

Whole-mount, free-floating tissues were washed in 50 mM KPBS, incubated with 0.3% $H_2O_2$ for 30 min, rinsed in 50 mM KPBS, and incubated in diluent (50 mM KPBS, 0.4% Triton X100, 1% bovine serum albumin, and 1% normal goat serum) for 30 min at 22° C. The tissues were then stained with OFQ-purified antibodies diluted 1:2000 to 1:4000 in the same diluent for 48 hours at 4° C. Tissues were washed in 50 mM KPBS with 0.02% Triton X-100, incubated with biotinylated goat anti-rabbit IgG, diluted 1:200 in diluent for 1 hour at 22° C., followed by incubation with avidin-biotin complex coupled to horseradish peroxidase 1:200 for 1 hour at 22° C. The horseradish peroxidase reaction product was made visible with 0.04% 3,3'-diaminobezidine tetrahydrochloride, 2.5% nickel chloride, and 0.01% $H_2O_2$ dissolved in 0.1 M sodium acetate. The reaction was terminated with two consecutive NaCl (0.9%) washes. The free-floating tissues were mounted on gelatin-coated slides treated with graded alcohol and xylene and coverslipped with Permount. Tissues were examined with a Zeiss Axiophot microscope. Immunohistochemical controls were performed by preabsorption and coincubation of OFQ antiserum with 4 mM to 10 mM of the antigen to which the antisera were made. Controls of the secondary antibody cross-reactivity were performed by omitting the primary antiserum.

The immunohistochemical results showed that numerous nerve fibers were immunoreactive in the myenteric plexus and circular muscle layer in the rat colon (data not shown). These immunoreactive fibers often surround nonimmunoreactive cell bodies. Occasionally, nerve cell bodies in the colon myenteric plexus are found to be immunoreactive. They appear to have the morphological characteristics of Dogiel type I neurons.

From the above, it should be clear that OFQ induced contractions only in the colon by in vitro studies from various regions of rat GI tract. OFQ up to a concentration of $10^{-6}$ M failed to elicit significant contractions in the longitudinal and circular muscle layer from the stomach and small intestine. Contractions induced by OFQ in the longitudinal muscle of the proximal colon were much greater than those in the distal colon. Therefore, the main site of contractile action of OFQ is suggested to be the proximal colon. The data revealed that OFQ caused various types of muscular contractions in rat proximal colon.

An in vivo study demonstrated that the intravenous administration of OFQ (3 pmol/kg-3 nmol/kg) significantly increased muscular contractions in the proximal colon but not in the stomach in rats. Furthermore, OFQ (1 nmol/kg, sc) significantly accelerated the colonic transit without affecting the gastrointestinal transit in rats, while structurally resembled dynorphin A (100 nmol/kg,sc) delays colonic transit (data not shown).

I claim:

1. A method of treatment, comprising:

a) providing:

i) a human having symptoms of an intestinal disorder; and ii) a therapeutic preparation comprising a neuropeptide having the amino acid sequence of SEQ ID NO:1; and b) administering said therapeutic preparation to said human.

2. The method of claim 1, wherein said intestinal disorder is post-operative ileus.

3. The method of claim 1, wherein said intestinal disorder is constipation.

4. The method of claim 1, wherein said intestinal disorder is irritable bowel syndrome.

5. The method of claim 1, wherein said human is a child.

6. The method of claim 1, wherein said preparation is administered orally.

7. A method of treatment, comprising:
a) providing:
   i) an animal having symptoms of an intestinal disorder; and
   ii) a therapeutic preparation comprising a neuropeptide having the amino acid sequence of SEQ ID NO:1; and
c) administering said therapeutic preparation to said animal.

8. The method of claim 7, wherein said animal is a horse.

9. The method of claim 8, wherein said horse has symptoms of post-operative ileus.

10. The method of claim 9, wherein said preparation is adminstered orally.

11. A suppository comprising a neuropeptide having the amino acid sequence of SEQ ID NO:1.

* * * * *

UNITED STATES PATENT AND TRADEMARK OFFICE
CERTIFICATE OF CORRECTION

PATENT NO. : 5,929,035
DATED : July 27, 1999
INVENTOR(S) : Chung Owyang

It is certified that error appears in the above-identified patent and that said Letters Patent is hereby corrected as shown below:

In column 8, line 28, please delete "$10^{-9}M-10-6M$" and insert -- $10^{-9}M-10^{-6}M$ --.

In column 8, line 44 please delete "$10_{-6}M$" and insert -- $10^{-8}M$ --.

In column 9, line 10 please delete" $>5 \times 10-6\ M$" and insert -- $>5 \times 10^{-6}M$ --.

In column 9, line 15, please delete "$10-5M$" and insert -- $10^{-5}M$ --.

In column 9, line 30, please delete "neurotransmitters,three" and insert -- neurotransmitters, three".

Signed and Sealed this

Eleventh Day of April, 2000

Attest:

Attesting Officer

Q. TODD DICKINSON

Director of Patents and Trademarks